US012778397B2

(12) United States Patent
Sekowski

(10) Patent No.: US 12,778,397 B2
(45) Date of Patent: Nov. 3, 2026

(54) CONTROLLABLE MICRO-ENDOSCOPE

(71) Applicant: Research and Development International Corp. (RDI), Pasadena, CA (US)

(72) Inventor: Marek G. Sekowski, Northwest Gig Harbor, WA (US)

(73) Assignee: RESEARCH AND DEVELOPMENT INTERNATIONAL CORP. (RDI), Pasadena, CA (US)

( * ) Notice: Subject to any disclaimer, the term of this patent is extended or adjusted under 35 U.S.C. 154(b) by 721 days.

(21) Appl. No.: 18/077,602

(22) Filed: Dec. 8, 2022

(65) Prior Publication Data

US 2024/0188807 A1 Jun. 13, 2024

(51) Int. Cl.
*A61B 1/005* (2006.01)
*A61M 25/01* (2006.01)

(52) U.S. Cl.
CPC .......... *A61B 1/0055* (2013.01); *A61B 1/0057* (2013.01); *A61M 25/0138* (2013.01)

(58) Field of Classification Search
CPC ..... A61B 1/005; A61B 1/0052; A61B 1/0055; A61B 1/0057; A61B 1/00071; A61B 2017/00309; A61M 25/0138
See application file for complete search history.

(56) References Cited

U.S. PATENT DOCUMENTS 4,723,936 A 2/1988 Buchbinder
5,827,278 A 10/1998 Webster, Jr.
5,921,978 A 7/1999 Thompson
6,746,422 B1 6/2004 Noriega
6,749,560 B1 * 6/2004 Konstorum ........ A61B 1/00071 604/525
6,926,711 B2 8/2005 Lentz
6,945,956 B2 9/2005 Waldhauser
7,381,198 B2 6/2008 Noriega
8,052,597 B2 * 11/2011 Boulais ................ A61B 1/0057 600/141
8,401,673 B2 3/2013 Bowe
8,403,867 B2 3/2013 Nowak
8,728,075 B2 5/2014 Wu
8,827,948 B2 9/2014 Romo
9,999,748 B2 6/2018 Cajamarca
10,029,073 B2 7/2018 Kabe
10,307,043 B2 * 6/2019 Rutgers .................. A61B 1/005
10,569,053 B2 2/2020 Gonzalez
11,116,938 B2 9/2021 Leeflang
2010/0179512 A1 7/2010 Chong
2010/0312056 A1 * 12/2010 Galperin .............. A61B 1/0051 600/141

(Continued)

FOREIGN PATENT DOCUMENTS

CA 2296290 A1 2/1999
EP 1465697 B1 7/2008

(Continued)

*Primary Examiner* — Ryan N Henderson
(74) *Attorney, Agent, or Firm* — Ladas & Parry, LLP

(57) ABSTRACT

A controllable endoscope comprising a tube cut out radially to form at least three long segments having each loops for slidably receiving pull wires, separated by series of short segments having no loops; all the segments being attached to each other only by portions of the tube that were not cut out.

1 Claim, 10 Drawing Sheets

(56) References Cited

U.S. PATENT DOCUMENTS

| | | | | |
|---|---|---|---|---|
| 2012/0024099 | A1* | 2/2012 | Main | A61B 17/0218 74/479.01 |
| 2012/0277730 | A1* | 11/2012 | Salahieh | A61B 90/10 604/528 |
| 2013/0047757 | A1* | 2/2013 | Okamoto | A61B 1/0016 74/89.22 |
| 2014/0052109 | A1 | 2/2014 | Organ | |
| 2014/0379000 | A1* | 12/2014 | Romo | A61B 17/29 606/130 |
| 2015/0335383 | A9 | 11/2015 | Cohen | |
| 2015/0366445 | A1* | 12/2015 | Rutgers | A61B 1/2676 128/200.26 |
| 2017/0105715 | A1* | 4/2017 | Kasic, II | A61B 17/00234 |
| 2018/0001058 | A1 | 1/2018 | Schlesinger | |
| 2018/0028177 | A1 | 2/2018 | Van Oepen | |
| 2018/0296798 | A1* | 10/2018 | Lepak | A61M 25/0136 |
| 2019/0209206 | A1* | 7/2019 | Patel | A61D 1/02 |
| 2020/0038128 | A1 | 2/2020 | Joseph | |
| 2020/0237189 | A1* | 7/2020 | Do | A61B 1/0011 |
| 2021/0113199 | A1 | 4/2021 | Lorenzo | |
| 2021/0307766 | A1* | 10/2021 | Keating | A61B 17/22 |
| 2022/0087505 | A1* | 3/2022 | Hirata | G02B 23/24 |
| 2022/0152355 | A1* | 5/2022 | Dolendo | A61M 25/0138 |
| 2022/0338718 | A1* | 10/2022 | Van Ness | A61B 1/0055 |
| 2022/0347936 | A1* | 11/2022 | Sekido | A61B 1/00073 |
| 2023/0128263 | A1* | 4/2023 | Major | A61M 25/0147 606/130 |
| 2023/0165446 | A1* | 6/2023 | Dolan | A61B 1/008 600/142 |
| 2024/0138660 | A1* | 5/2024 | Horie | A61B 1/0056 |
| 2024/0245284 | A1* | 7/2024 | Thissen | A61M 25/0147 |
| 2024/0260820 | A1* | 8/2024 | Ku | A61B 1/0055 |
| 2024/0407772 | A1* | 12/2024 | Gafford | A61M 25/0138 |
| 2025/0049305 | A1* | 2/2025 | Thissen | A61M 25/0138 |

FOREIGN PATENT DOCUMENTS

| | | | |
|---|---|---|---|
| EP | 1709987 | B1 | 12/2009 |
| EP | 2147694 | A1 | 1/2010 |
| EP | 2470097 | B1 | 4/2016 |

* cited by examiner

CONTROLLABLE MICRO-ENDOSCOPE

TECHNICAL FIELD

This presentation relates to endoscopes; in particular controllable endoscopes that have at least a portion that can be remotely and controllably bent by a user; in particular controllable endoscopes having a diameter of two millimeters or less.

BACKGROUND

An endoscope is an instrument for examining the interior of the body, that generally comprises a flexible tube with a source of light to illuminate the interior site to be examined, as well as visualization means to visualize the interior site. Both the source of light and visualization means can be localized at a distal end of the endoscope and electrically connected to a proximal end of the endoscope, or they can be located beside the proximal end of the endoscope and connected to optical fibers bringing light to and from the distal end of the endoscope. Surgical instruments can be attached to the distal end of an endoscope and can be controllable from the proximal end of the endoscope to conduct a biopsy or surgery. Endoscopes are used as a non-invasive or minimally invasive tool for diagnosis or treatment. There exists a need for endoscopes having a diameter as reduced as possible, to allow the endoscope to be as little invasive as possible.

Preferably, at least a distal portion of an endoscope can be bent remotely in a controllable manner to allow the user to move the distal portion in a desired manner, thus easing the operation of the endoscope. It is known to remotely bend a distal portion of an endoscope in a controllable manner by forming said distal portion as a series of coaxial segments of same diameter attached to each other by pairs of radial hinges, where at least one pull-wire has a distal end attached to the distal end of the endoscope, passes through a loop of each segment, and has a proximal end that can be pulled from the proximal end of the endoscope. Pulling the wire asymmetrically pulls the attached side of the distal end of the endoscope closer to the proximal end of the endoscope, resulting in the segments radially rotating with respect to each other and bending the distal portion of the endoscope.

FIG. 1 illustrates a distal portion 10 of a known endoscope having a distal end 12 (which can also be the distal end of the endoscope) and a proximal end 14, which can be connected to a proximal portion of the endoscope (not shown) that comprise the proximal end of the endoscope (not shown). Distal portion 10 comprises a series of concentric segments 16 attached to each other by pairs of radial hinges 18. The inner walls 19 of the series of segments 18 form a lumen having an axis concentric with each segment. In the illustration, each radial hinge 18 of a segment comprises a half-circle protrusion 20 of the segment that passes over the next segment, and a rivet 22 perpendicular to the axis of the tube that pivotally assembles the segment protrusion to the next segment. The figure only shows the hinges 18 arranged on a top of portion 10. Diametrically arranged hinges 18 (not shown) can be found on a bottom of portion 10. Each segment 16 also comprises a left loop 24 and a right loop 26 protruding inside the lumen. The left loops 24 of the series of segments 16 are aligned such that a left pull wire (not shown) having a distal end secured to a left side of the distal end 12 can slidably pass through each of the loops 24 and pull the left side of distal end 12 when a proximal end of the left pull wire is pulled. Similarly, the right loops 26 of the series of segments 16 are aligned such that a right pull wire (not shown) having a distal end secured to a right side of the distal end 12 can slidably pass through each of the loops 26 and pull the right side of distal end 12 when a proximal end of the right pull wire is pulled. A problem with the structure of FIG. 1 is that it becomes extremely complex and expensive to build if the diameter of the endoscope becomes smaller than 5 mm.

There exists a need for a controllable endoscope structure suitable for manufacturing endoscopes with a diameter smaller than 5 mm; preferably smaller than 2 mm.

SUMMARY

Embodiments of this presentation provides for a controllable endoscope comprising a tube cut out radially to form at least three long segments having each loops for slidably receiving the pull wires, separated by series of short segments having no loops; all the segments being attached to each other only by section of the tube (or "attachment sections") that were not cut out. According to embodiments of this presentation, the long segments comprise each a left loop and a right loop for slidably receiving respectively a left and a right pull wire, and the axial lengths of the short and long segments, along with the axial lengths of the radial cuts, are chosen such that the left and right pull wires always remain each on a left side and a right side of a sheet of points passing through all the attachment sections that bend when the pull wires are pulled.

According to embodiments of this presentation, a proximal portion of each of the pull wires, between the most proximal of the long segments and a proximal end of the endoscope, passes through a respective compression coil such that pulling the proximal end of each pull-wire with respect to a proximal end of the respective compression coil pulls the distal end of the pull wire toward a distal end of the respective compression coil, which is fixedly attached with respect to a respective loop in the most proximal of the long segments.

Embodiments of this presentation comprise a controllable endoscope with a hollow tube having a distal end and a proximal end, the hollow tube comprising a tube wall surrounding a tube lumen having a lumen axis; a controllable section of the tube comprising an alternance of long-segments of the tube and flexible sections of the tube wherein: the long-segments of the tube comprise a distal long-segment, a proximal long-segment, and n intermediate long-segments, with n being an integer at least equal to 1; each long-segment having a first axial length; wherein in each flexible section the tube wall comprises a plurality of cuts along a series of planes perpendicular to the lumen axis, the cuts being arranged such that the tube wall forms a series of short-segments of the tube, each attached to the next and previous segments of the tube by at least one attachment section of the tube, the at least one attachment section of the tube comprising at least one radial portion of the tube wall in the same plane as said cut but not removed by said cut; each attachment section having a second axial length and each short-segment of the tube having a third axial length, wherein the first axial length is equal to or greater than three times the third axial length plus two times the second axial length; wherein the n intermediate long-segments and the proximal long-segment comprise each at least one loop structure protruding from the tube wall into the lumen, each loop structure having a loop opening parallel to the lumen axis, arranged to form at least one series of loop openings aligned in a direction parallel to the lumen axis when the controllable section of the tube is in an unbent state; and wherein at least one tensioning wire having a distal end and a proximal end slidingly passes through the opening of the at least one series of loop structures, the distal end of the at least one tensioning wire being secured inside the lumen to the distal long-segment of the tube, such that controllably pulling the proximal end of the tensioning wire results in controllably bending the controllable section of the tube by flexing said attachment sections.

According to embodiments of this presentation, said cuts are wedge-shaped, whereby an axial length of each short segment of the tube varies radially. According to embodiments of this presentation, the cuts follow parallel planes, whereby each short segment has a constant axial length. According to embodiments of this presentation, the cuts separating the segments have each an axial length such that, by bending the attachment sections separating two consecutive segments, radial planes perpendicular to the axis of the lumen of each segment, respectively, can be rotated by up to three degrees with respect to each other.

According to embodiments of this presentation, the plurality of cuts are arranged such that the least one attachment section of the tube that attaches each segment to the next and previous segments comprises a pair of radial portions of the wall diametrically opposed with respect to the lumen axis.

According to embodiments of this presentation, the plurality of cuts are arranged such that the pairs of radial portions of the wall that attach two successive segments have radial positions rotated 90 degrees with respect to each other.

According to embodiments of this presentation, said at least one series of loop openings aligned in a direction parallel to the lumen axis comprise a pair of diametrically opposed series of loop openings aligned in directions parallel to the lumen axis; wherein the at least one tensioning wire comprises a pair of tensioning wires having each a distal end and a proximal end, each tensioning wire respectively passing in the openings of one of said diametrically opposed series of loop openings, the distal end of each tensioning wire being secured inside the lumen to the distal long-segment of the tube such that controllably pulling respectively the proximal end of a first one and a second one of the pair of tensioning wires results in controllably bending the controllable section of the tube in first and second diametrically opposed directions.

According to embodiments of this presentation, the hollow tube comprises a proximal section between the proximal long-segment and the proximal end; and said tensioning wire passes through a compression coil arranged in the lumen between the loop opening of the at least one loop structure of the proximal long-segment and the proximal end of the tube.

According to embodiments of this presentation, the controllable endoscope further comprises means for controllably pulling the proximal end of the tensioning wire with respect to a proximal end of said compression coil.

According to embodiments of this presentation, the proximal section of the tube is flexible.

According to embodiments of this presentation, the proximal section of the tube comprises a series of cuts having each a radial length smaller than a perimeter of the tube.

According to embodiments of this presentation, said means for controllably pulling the proximal end of the tensioning wire comprise a lever having a pivotal axis and a radius, an actuating end with a groove perpendicular to said radius, and a hole with an axis perpendicular to said radius, arranged such that the tensioning wire passes in the groove of the actuating end and is bent 180 degree such that the proximal end of the tensioning wire passes through said hole; a peg being secured in the hole to maintain the tensioning wire in position; wherein when the lever pivots around said axis in a first direction the lever pulls the tensioning wire and when the lever pivots around said axis in a second direction the tensioning wire slacks; said groove having a depth provided to prevent the slacking wire from exiting the groove.

According to embodiments of this presentation, the compression coil extends proximally beyond the proximal end of the tube, and comprises a curved section between the proximal end of the tube and the proximal end of the compression coil; said curved section having a curvature arranged to freely change if the compression coil gets compressed when pulling the proximal end of the tensioning wire.

According to embodiments of this presentation, the loop openings and the attachment sections have different radial positions, such that pulling the proximal end of the tensioning wire results in bringing closer portions of the segments of the tube, separated by the cuts when the tube is in an unbent state and that have a same axial position as the loop openings, by flexing the attachment sections between the segments of the tube.

According to embodiments of this presentation, the controllable section of the tube is arranged to achieve a maximally bent state when the attachment sections between the segments of the tube are flexed sufficiently to let portions of segments of the tube that have a same axial position as the loop openings, touch each other instead of being separated by the cuts.

According to embodiments of this presentation, a distance between successive loop openings, or between the secured distal end of the at least one tensioning wire and a closest loop opening, when the controllable section of the tube is in an unbent state, is chosen so that the tensioning wire remains on a same side of a sheet of points which includes the attachment sections that flex when bending the controllable section of the tube from an unbent state to the maximally bent state.

According to embodiments of this presentation, the sheet of points includes the axis of the lumen, and a maximal distance S, between successive loop openings, or between the secured distal end of the at least one tensioning wire and a closest loop opening, when the controllable section of the tube is in an unbent state, is $S=2\pi R(2\theta/360°)$; where $\theta=\sin^{-1}[(X/2)/(R+r)]$; and $X=2\sqrt{(R+r)^2-(R+r/2)^2}$; with R being the radius of a maximal bend of a line following the lumen axis of each segment of the tube, and r being the radius of the controllable section.

Embodiments of this presentation, comprise a tube cut out radially to form at least three long segments having each loops for slidably receiving pull wires, said at least three long segments separated by series of short segments having no loops; all the segments being attached to each other only by portions of the tube that were not cut out.

According to embodiments of this presentation, axial lengths of the short and long segments, along with axial length of the radial cuts, are chosen such that the pull wires always remain on a same side of a sheet of points which includes the attachment sections of the tube that flex when the pull wires are pulled to bend the controllable endoscope.

These and other features and advantages will become further apparent from the detailed description and accompanying figures that follow. In the figures and description, numerals indicate the various features; like numerals referring to like features throughout both the drawings and the description.

The figures are not necessarily to scale.

DETAILED DESCRIPTION

In the following description, numerous specific details are set forth to clearly describe various specific embodiments disclosed herein. One skilled in the art, however, will understand that the presently claimed invention may be practiced without all of the specific details discussed below. In other instances, well known features have not been described so as not to obscure the invention.

Figure 2:
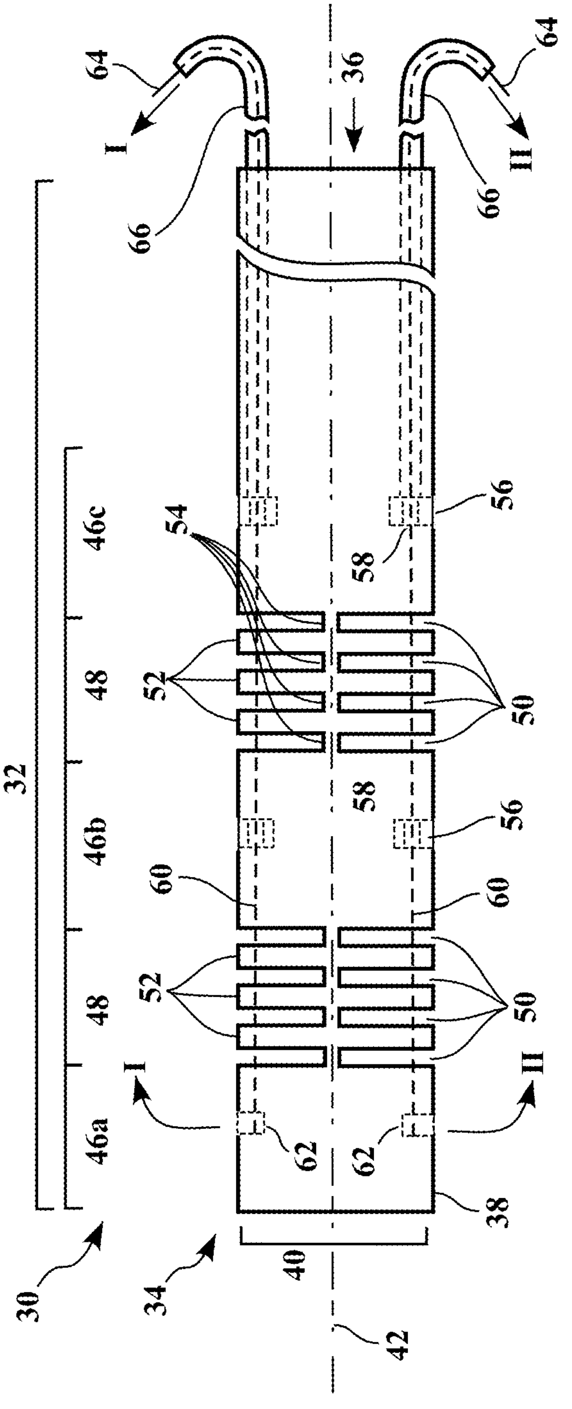
FIG. 2 illustrates schematically a controllable endoscope according to embodiments of this presentation.

FIG. 2 illustrates schematically a controllable endoscope 30 according to embodiments of this presentation, comprising a hollow tube 32 with a distal end 34 and a proximal end 36, the hollow tube 32 comprising a tube wall 38 surrounding a tube lumen 40 having a lumen axis 42; a controllable section 44 of the tube comprising an alternance of long-segments 46 of the tube and flexible sections 48 of the tube. According to embodiments of this presentation, there are at least three long-segments 46 of the tube: a distal long-segment 46*a*, a proximal long-segment 46*c*, and n intermediate long-segments 46*b*, wherein n is an integer at least equal to 1. A single intermediate long-segment 46*b* is illustrated in FIG. 2. According to embodiments of this presentation, each flexible section 48 comprises a plurality of cuts 50 that each completely remove a portion of the tube wall 38 along a series of planes (not shown) perpendicular to the lumen axis 42. According to embodiments of this presentation, the cuts 50 are arranged such that the tube wall 38 forms a series of short-segments 52 of the tube, each segment attached to the next and previous segments of the tube by at least one attachment section 54 of the tube formed by the radial portions of the tube wall 38 in the same plane as the cuts 50, that were not removed by said cuts.

Figure 1:
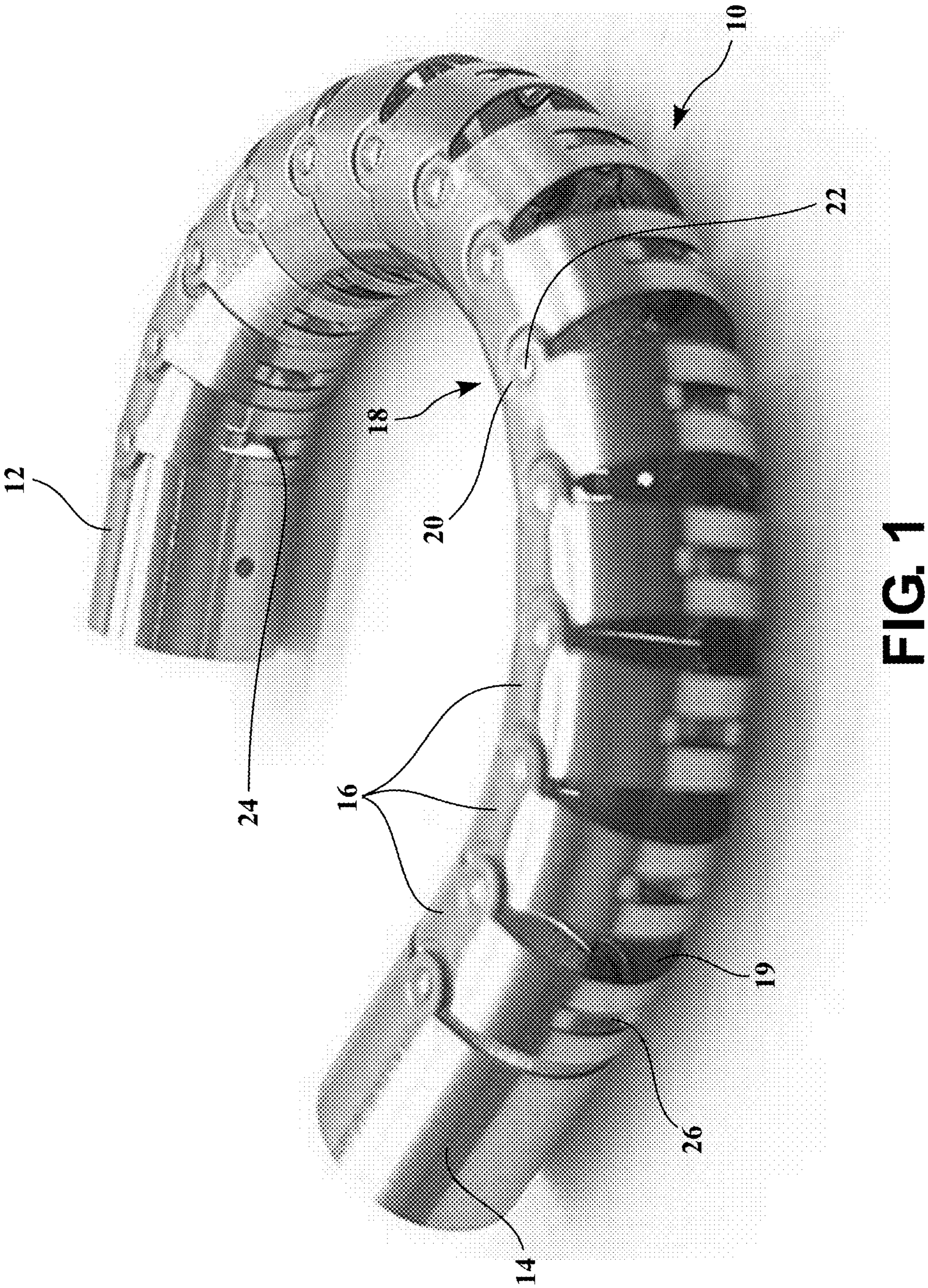
FIG. 1 shows a known distal portion of a controllable endoscope.

According to embodiments of this presentation, each long-segment 46 of the tube has an axial length that is larger than or equal to three times the axial length of a short segment 52 plus two times the axial length of a cut/an attachment section. According to embodiments of this presentation, the cuts separating the segments have each an axial length such that, by bending the attachment sections separating two consecutive segments, radial planes perpendicular to the axis of the lumen of each segment, respectively, can be rotated by one to three degrees with respect to each other, along a radial rotation axis passing through said attachment sections. According to embodiments of this presentation, multi-part hinges or pivots (such as using a rivet 22 in FIG. 1) providing for a large angular rotation between relatively long tube segments are replaced by attachment sections between a multitude of shorter tube segments, which rely on the resilience of the tube material at the attachment sections to provide each a small angle rotation between the shorter tube segments. In the illustration of FIG. 2, the cuts 50 have parallel edges, as would be formed by an abrasive disc having parallel sides. In practice, the cuts can have an axial length of the order of 10 to 100 microns and can be made using laser or chemical etching. According to an embodiment, an example of the radial length of the attachment sections can be of 100 to 200 microns. With such parallel cuts, the segments 52 and 46 formed by the cuts have a constant axial length. However, in other embodiments of this presentation, the cuts 50 have non parallel edges, as would be formed by an abrasive disc having non parallel sides, and the segments 52 and 46 formed by the cuts have a variable axial length, longest in the vicinity of the attachment sections 54.

According to embodiments of this presentation, the segments 52 and 46, or 52 and 52, can be attached to each other by a single attachment section 54. According to embodiments of this presentation, the segments 52 and 46, or 52 and 52, can be attached to each other by a pair of attachment sections 54 diametrically arranged with respect to the lumen axis 42. Assuming that FIG. 2 shows a top view of endoscope 30, the attachment sections 54 shown are top attachment sections and endoscope 30 also comprises bottom attachment sections (not shown) arranged symmetrically from top attachment sections 54 with respect to axis 42.

According to embodiments of this presentation, the n intermediate long-segments (one shown with reference 46*b*) and the proximal long-segment 46*c* comprise each at least one loop structure 56 protruding from the tube wall 38 into the lumen 40, each loop structure 56 having a loop opening 58 parallel to the lumen axis 42. According to embodiments of this presentation, each loop structure has an axial length that is at least the same as the axial length of a short segment. According to embodiments of this presentation, the loop openings 58 are arranged to form at least one series of loop openings aligned in a direction parallel to the lumen axis 42 when the controllable section of the tube is in an unbent state. According to embodiments of the presentation, and as illustrated in FIG. 2, each of the n intermediate long-segments (46*b* shown) and the proximal long-segment 46*c* comprise a pair of loop structures 56 forming a pair of series of loop openings aligned in directions parallel to the lumen axis diametrically opposed with respect to the lumen axis 42.

According to embodiments of this presentation, at least one tensioning wire 60 having a distal end 62 and a proximal end 64 is arranged to slidingly pass through the openings 58 of the at least one series of loop structures; wherein the distal end 62 of the at least one tensioning wire 60 is secured inside the lumen 40 to the distal long-segment 46*a* of the tube such that controllably pulling (Arrows I, II) the proximal end 64 of the tensioning wire results in controllably bending the controllable section 44 of the tube. As illustrated in FIG. 2, according to embodiments of this presentation the at least one tensioning wire 60 comprises a pair of tensioning wires 60 having each a distal end 62 and a proximal end 64, each tensioning wire 60 respectively passing in the openings 58 of one of the diametrically opposed series of loop openings, the distal end 62 of each tensioning wire 60 being secured inside the lumen 40 to the distal long-segment 46*a* of the tube such that controllably pulling (Arrows I, II) respectively the proximal end 64 of a first one and a second one of the pair of tensioning wires 60 results in controllably bending the controllable section 44 of the tube in first and second diametrically opposed directions (Arrows I', II').

According to embodiments of this presentation, the tube 32 comprises a proximal section between its proximal long-segment 46*c* and its proximal end 36; and said tensioning wires 60 pass each through the lumen 65 of a compression coil 66 itself arranged in the lumen 40 between the loop opening 58 of the at least one loop structure 56 of the proximal long-segment 46*c* and the proximal end 36 of the tube. A distal end 67 of compression coil 66 is attached to the at least one loop structure 56 of the proximal long-segment 46*c*, such that the wire 60 passes freely through the loop opening 58 and through the lumen 65.

Figure 3:
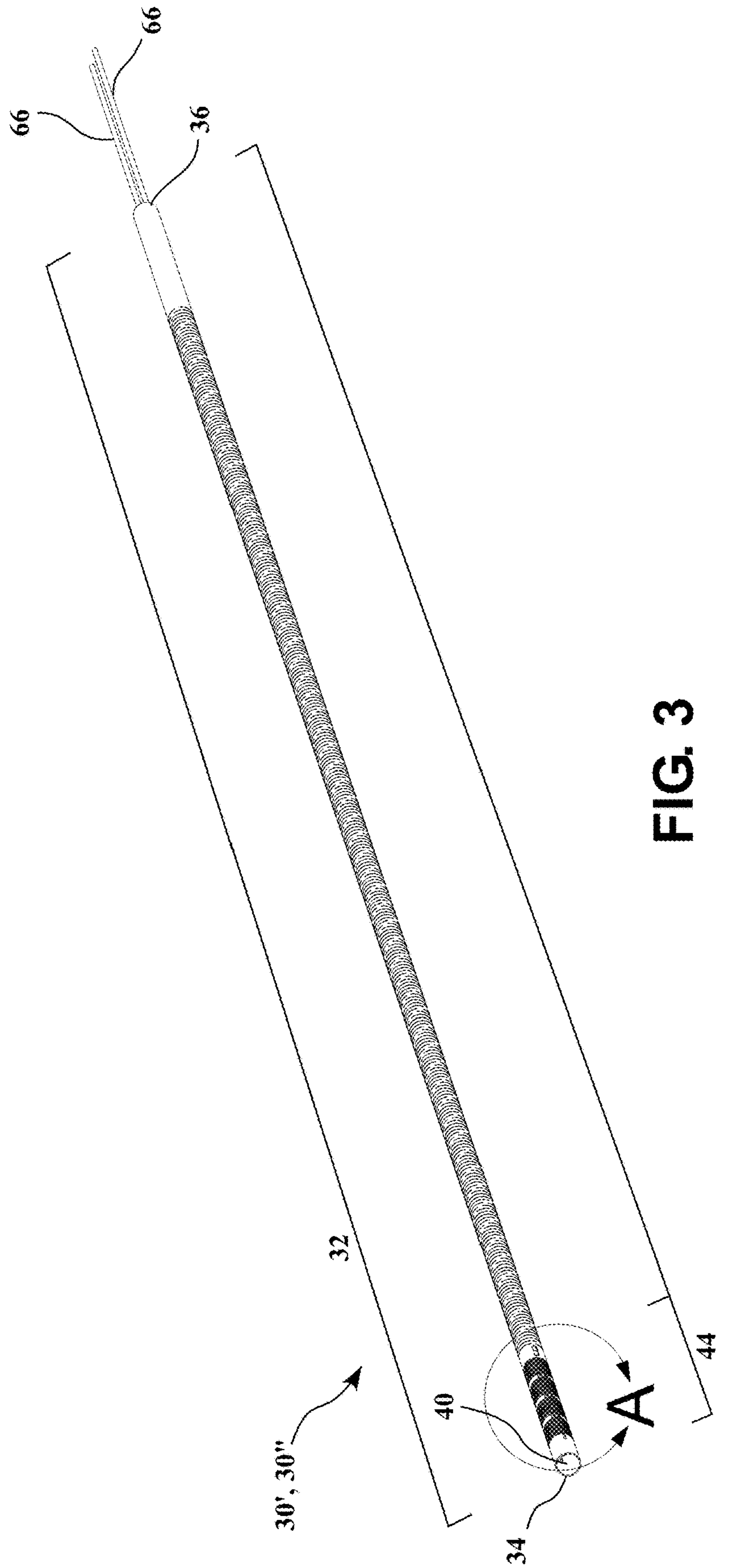
FIG. 3 illustrates schematically a controllable endoscope according to embodiments of this presentation.

FIG. 3 is an elevation view of a controllable endoscope 30' or 30" according to embodiments of this presentation that has essentially the same structure as controllable endoscope 30. In the embodiment illustrated in FIG. 3, the tube 32 comprises a proximal section 68 between its controllable section 44 and its proximal end 36, wherein said proximal section of the tube is made flexible by making in the tube a series of cuts having each a radial length smaller than a perimeter of the tube 32. According to embodiments of this presentation, the series of cut can comprise cuts of the same order of size as the cuts that form the small segments 52 of controllable section 44, to make at least a portion of proximal section 68 flexible. It is noted that compression coils 66 pass freely, in a generally parallel arrangement, through the tube lumen 40 in proximal section 68, just to be attached by their distal end 67 to the proximal long-segment 46*c*. The compression coils 66 allow tensioning the pull wires 66 in the controllable section 44 of the endoscope without exerting any significant tension in the proximal section 68. This feature allows controllably bending the controllable section 44 without introducing tensions in proximal section 68. Advantageously, when the endoscope is inserted in a bodily cavity of a patient, this feature allows the user to controllably bend the work end of the endoscope without creating discomfort to the user by making the proximal tension stiffer.

Figure 4:
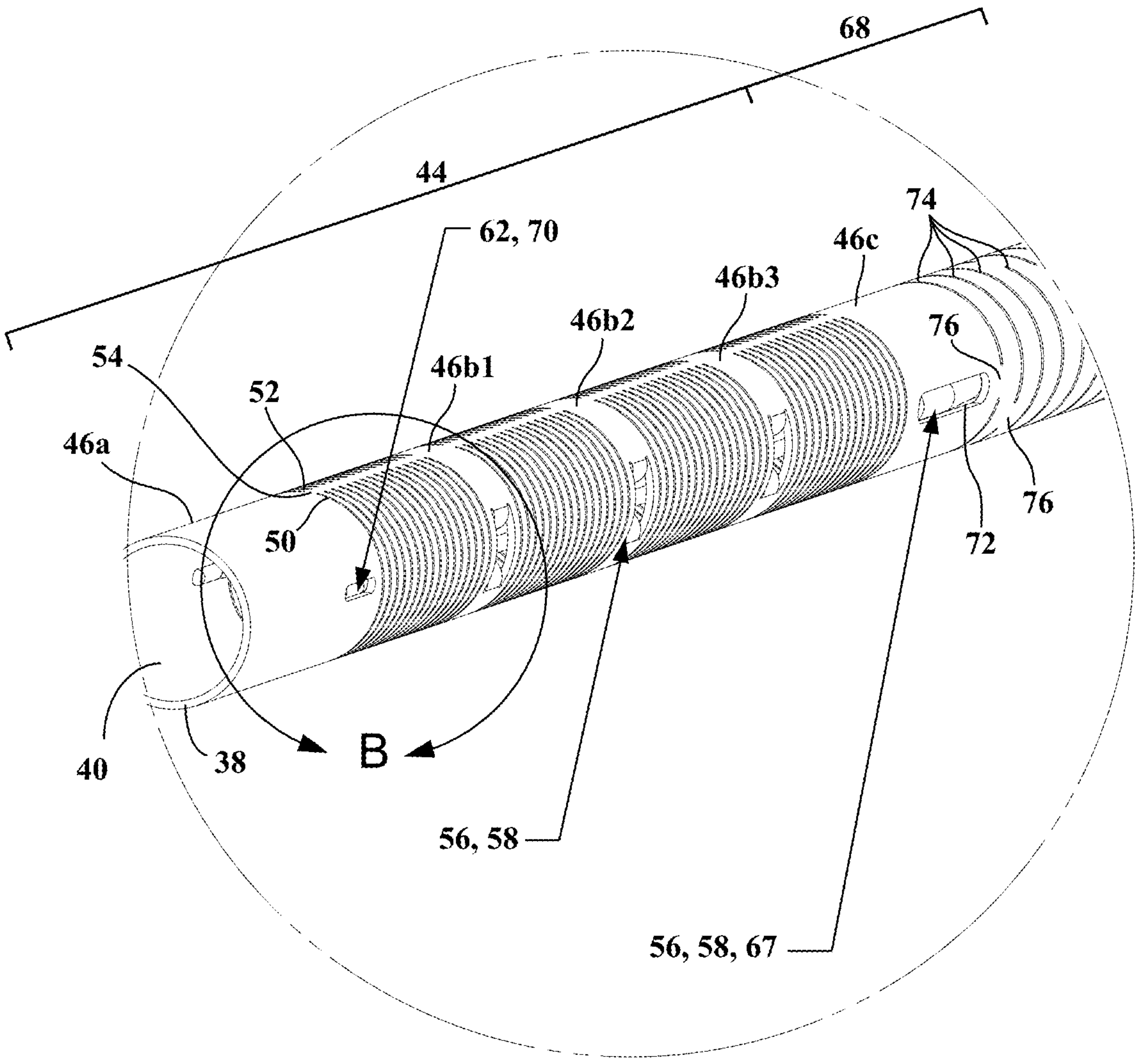
FIG. 4 illustrates in an enlarged manner an embodiment of the controllable endoscope of FIG. 3.

FIG. 4 illustrates in an enlarged manner a detail of an embodiment of the endoscope 30' of FIG. 3, within the circle referenced "A", which comprises three intermediate long-segments 46*b*1, 46*b*2, 46*b*3 identical each to the intermediate long-segment 46*b* shown in FIG. 2. According to embodiments of the present application, there are sixteen short segments between each long segments. According to embodiments of this presentation, and as illustrated in FIG. 4, the distal long-segment 46*a* and/or the proximal segment 46*c* can each be longer than the intermediate long-segments 46*bi*, with i=1 to n. As illustrated in FIG. 4, the attachment sections 54 attaching the segments together can be aligned together, at a radial position different from the radial position of the loop structures 56. In FIG. 4, the loop structures are formed to the left and right of the long-segments and the attachment sections 54 attach the segments by their top and bottom. According to embodiments of this presentation, the loop structures 56 (and the loop openings 58) and the attachment sections 54 have different radial positions, such that pulling the proximal end of the tensioning wires 60 results in bringing closer the portions of the segments of the tube, which are separated by the cuts when the tube is in an unbent state and that have a same axial position as the loop openings 58, by flexing the attachment sections 54 between the segments of the tube. All together, the attachment sections 54 form a sheet of points (not illustrated) that flexes but is not compressed when the attachment sections 54 are flexed. Said sheet of points comprise a plurality of parallel flexure axes materialized each by a pair of attachment sections 54. Said sheet of point can be seen as a neutral plane that is not compressed but is deformed into a cylindrical shape when the tube is bent by a pull wire.

The sheet of points is normal to a flexure plane (not illustrated) of the tube, which comprises the axis 42 of the lumen as well as the tensioning wires 60. According to embodiments of this presentation, the tube essentially flexes along the flexure plane when the tube is bent by flexing the attachment sections 54. According to embodiments of this presentation, each short-segment 52 of the tube has an axial length of the order of twice the thickness of the tube wall, for example for a tube in series 300 stainless steel with a tube wall that has a 75 micron thickness As illustrated in FIG. 4, each loop structures 56 in the long-segments can be made by cutting radially the tube wall 38 along two parallel short arcs, then pushing the portion of the tube wall 38 between the two short arc cuts toward the inside of the lumen so as to make said portion of the tube wall concave, thus forming the loop 58 of loop structure 56. According to embodiments of this presentation, loop structure 56 has an axial length of at least the axial length of a short-segment 52, and the remainder portions of the long-segments 46, on both side of the loop structure 56, have each an axial length at least equal to the axial length of a short-segment plus the axial length of one cut.

According to embodiments of this presentation, not shown in FIG. 4, the distal long-segment 46*a* and/or the proximal segment 46*c* can each have loop structures 56 in the same way as the intermediate long-segments 46*bi*. According to embodiments of this presentation, and as illustrated in FIG. 4, the distal long-segment 46*a* can dispense from the loop structures 56, for example by welding the distal ends 62 of the wires 60 to the tube wall of that section, through small holes 70 made in said tube wall. According to embodiments of this presentation, and as illustrated in FIG. 4, the loop structures 56 of the proximal long-segment 46*c* can alternatively be formed by welding a distal portion of the compression coils 66 to the tube wall of that section, for example through small holes 72 made in said tube wall. In that case the loop opening 58 of the loop structures % of the proximal long-segment 46*c* is formed by the lumen of the welded portion of the compression coil 66.

According to embodiments of this presentation, and as illustrated in FIG. 4, proximal section 68 is made flexible by radial cuts 74 separating the tube in sections held together by attachment sections 76 (one, two or more) where the cuts 74 have not removed the tube wall 38 completely. According to embodiments of this presentation, the successive attachment sections 76 have a different radial position. The radial position of the successive attachment sections can be a series of angles varying periodically along the length of proximal section 68 in a range of 0 to 360 degrees with respect for example to the position of a series of loop structures.

Figure 5:
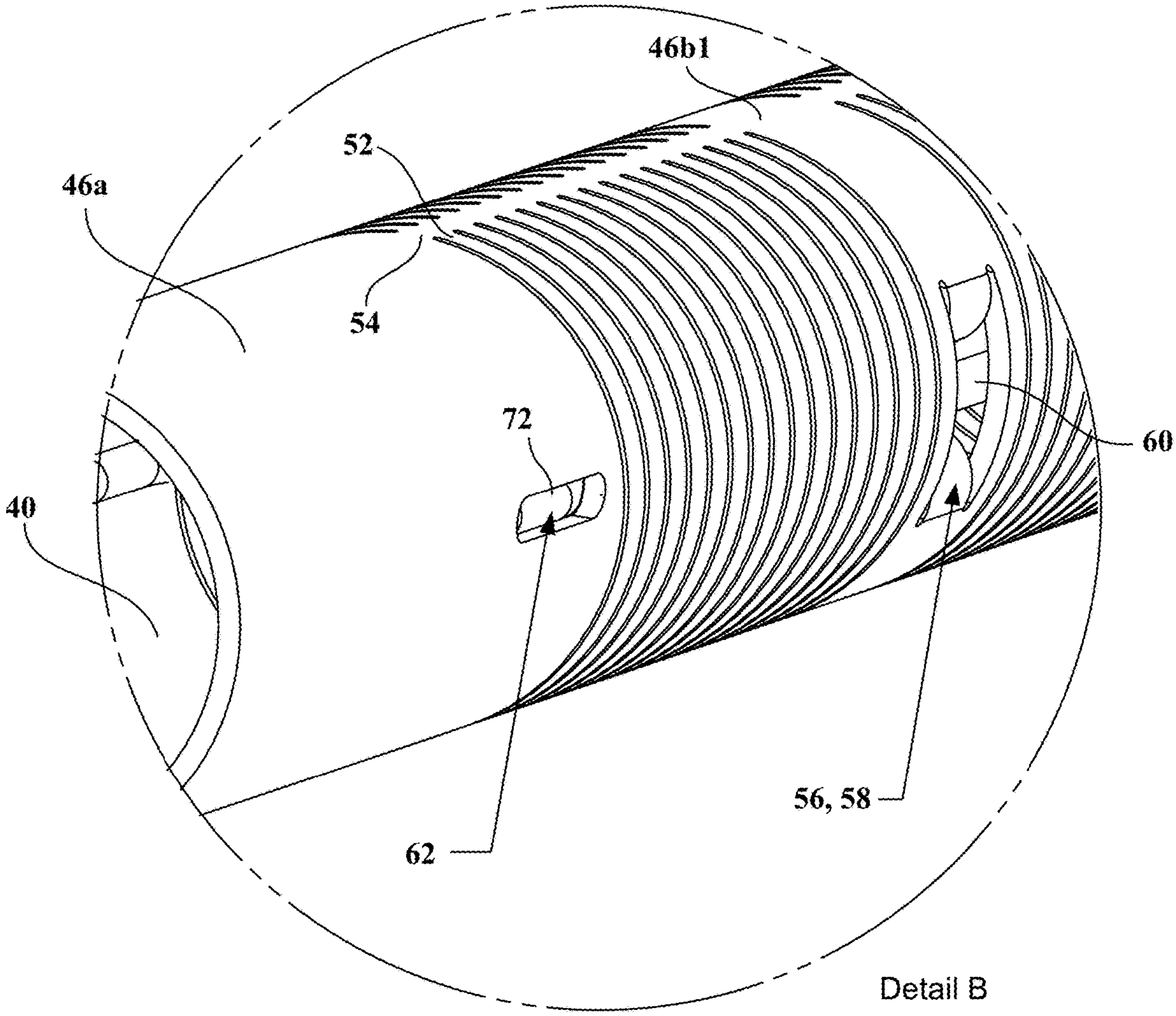
FIG. 5 illustrates in an enlarged manner a detail of the controllable endoscope of FIG. 4.

FIG. 5 illustrates in an enlarged manner the portion of the controllable endoscope of FIG. 4 that is within the circle referenced "B".

Figure 6:
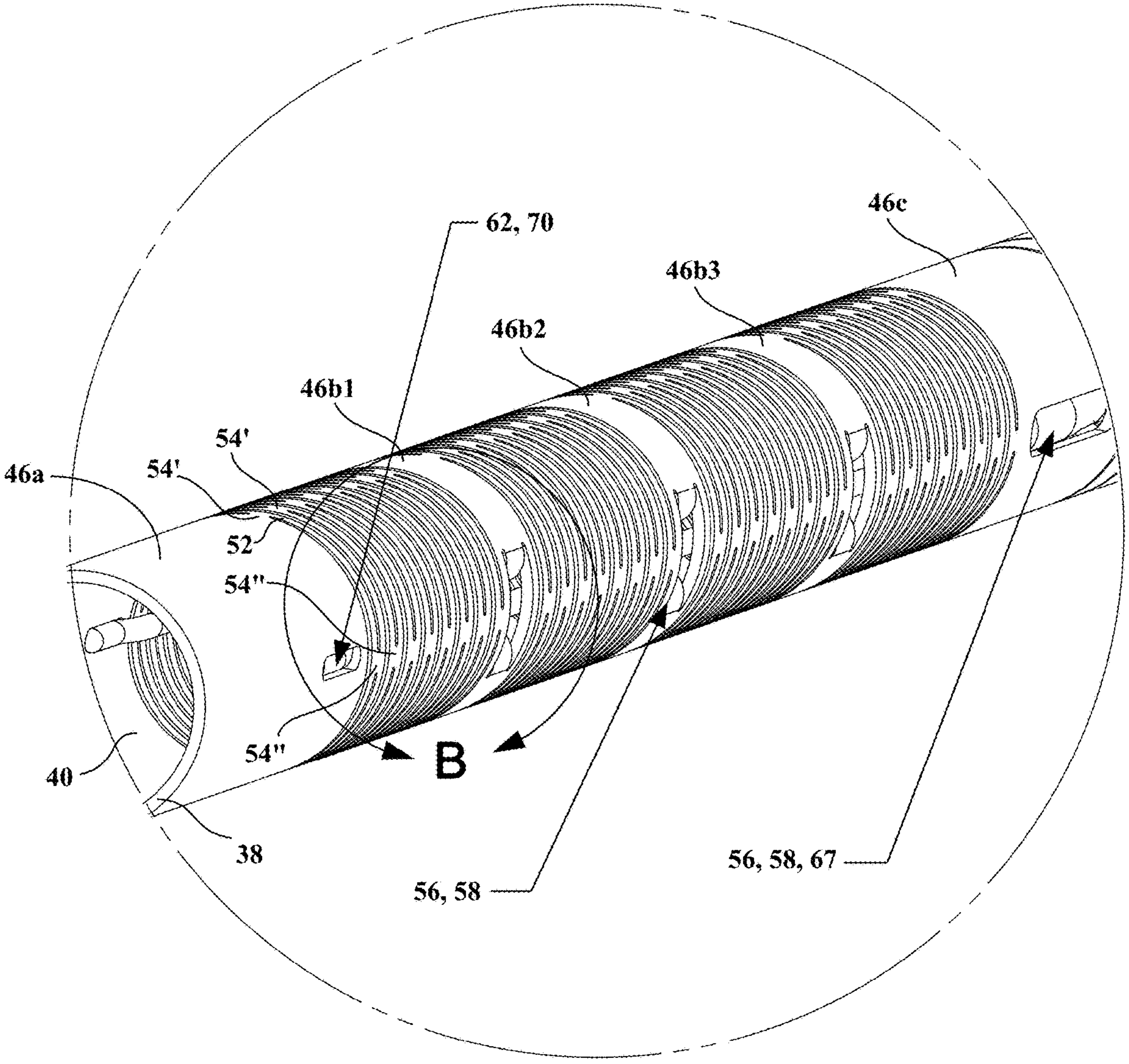
FIG. 6 illustrates in an enlarged manner an embodiment of the controllable endoscope of FIG. 3.

FIG. 6 illustrates schematically a detail of an alternative embodiment 30" of the endoscope 30' of FIG. 3, within the circle referenced "A". The embodiment 30" in FIG. 6 is essentially identical to the embodiment 30' of FIG. 4, except that the attachment sections 54', 54" attaching the segments together are arranged such that the pairs of attachment sections 54 which attach two successive segments have radial positions rotated 90 degrees with respect to each other. Another difference is that in the embodiment of FIG. 6, the cuts 50 have a wedge shape, i.e. do not have parallel edges, such that the cuts are shorter, radially close to the attachment sections 54 (54', 54" in FIG. 6), than at the point of the cut radially the farthest from the attachment sections. It follows that the segments of the tube have an axial length that varies radially. Wedge-shaped cuts can also be used in the embodiment illustrated in FIG. 4 and the parallel-shaped cuts illustrated in FIG. 4 can be used in the embodiment illustrated in FIG. 6.

Figure 7:
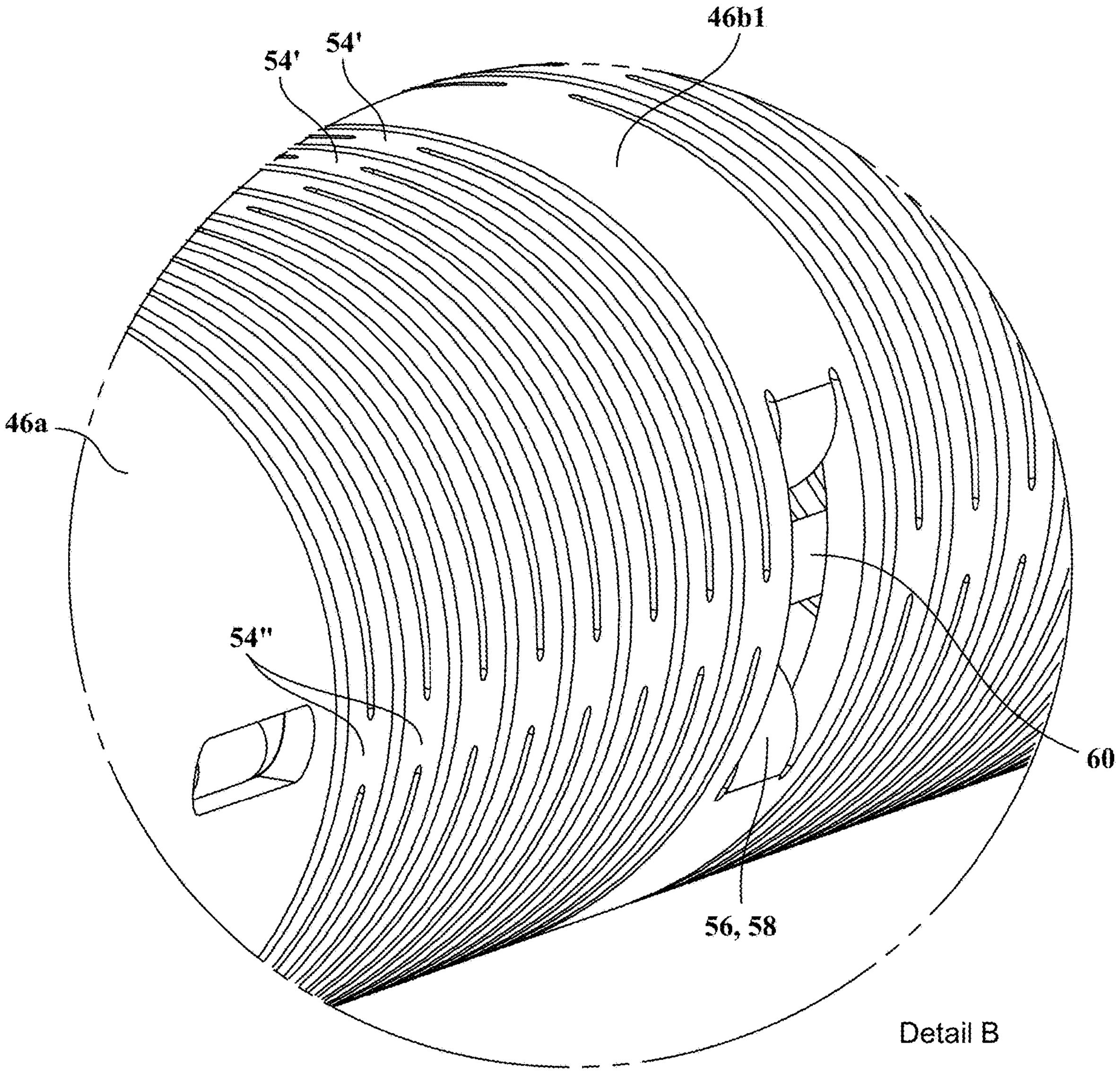
FIG. 7 illustrates in an enlarged manner a detail of the controllable endoscope of FIG. 6.

FIG. 7 illustrates in an enlarged manner the portion of the controllable endoscope of FIG. 4 that is within the circle referenced "B".

Figure 8:
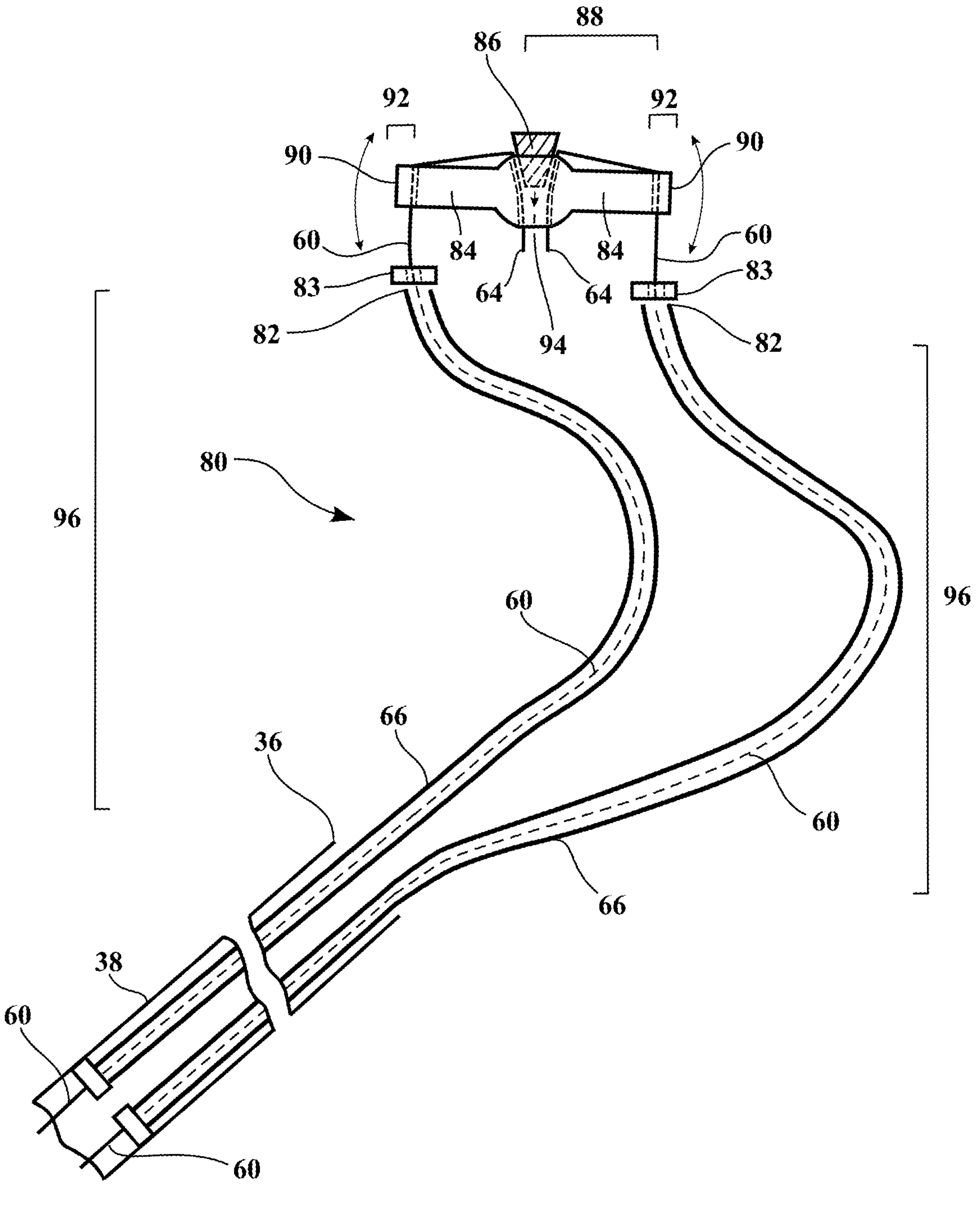
FIG. 8 illustrates a structure arranged to controllably pull the wires of the endoscopes of FIGS. 2 to 8.

FIG. 8 illustrates a structure 80 arranged to controllably pull the proximal portions 64 of the wires 60, each with respect to a proximal end 82 of said compression coil 66. According to embodiments of this presentation, the proximal end 82 of each compression coil 66 is secured to a loop structure 83 that prevents motion of the proximal end 82 when the wire 60 moves forward or backward in the lumen of the compression coil 66.

According to embodiments of this presentation, the structure comprises at least one lever 84 having a pivotal axis 86 and a radius 88, an actuating end 90 with a groove 90 perpendicular to said radius 88. Two levers 84 arranged symmetrically to axis 86 are shown in FIG. 8 to allow pulling on two wires 60 as illustrated in FIGS. 2 to 7. According to an embodiment, a hole 94 with an axis perpendicular to said radius 88 is arranged such that each tensioning wire 60 passes in the groove 90 of one of the actuating ends 90, then is bent 180 degree such that the proximal end 64 of the tensioning wire passes through said hole 94, and a peg is wedged and secured/glued in the hole to maintain the bent end 64 of the tensioning wire 60 in position. With the above arrangement, when the lever 84 pivots around the axis 86 in a first direction the lever 84 pulls the tensioning wire 60; and when the lever 84 pivots around axis 86 in a second, opposite direction, the tensioning wire 60 slacks. Preferably, groove 92 has a depth provided to prevent the slacking wire 60 from exiting the groove 92.

According to embodiments of this presentation, each compression coil 66 extends proximally beyond the proximal end of the tube, and comprises a curved section % between the proximal end 36 of the tube and the proximal end 82 of the compression coil 66. Said curved section 96 has a curvature arranged to freely change (i.e. to change without being restrained by other parts of the structure) if the compression coil 66 gets compressed when pulling the proximal end 64 of the tensioning wire 60. The Inventors have noted that compression coils may have manufacturing defects that make them slightly compressible. If such defect exists, a compression coil 66 can get compressed when the tensioning wire is pulled with respect to the end 82 of the compression coil. This may result in exerting an undesired bending strain on the flexible portion 68 of the endoscope. The Inventors have noted that providing a curved section 96 arranged as described above advantageously causes any eventual compression of the compression coil 66 to change the curvature of section 96 before any strain is exerted on the flexible portion 68 of the endoscope.

Figure 9:
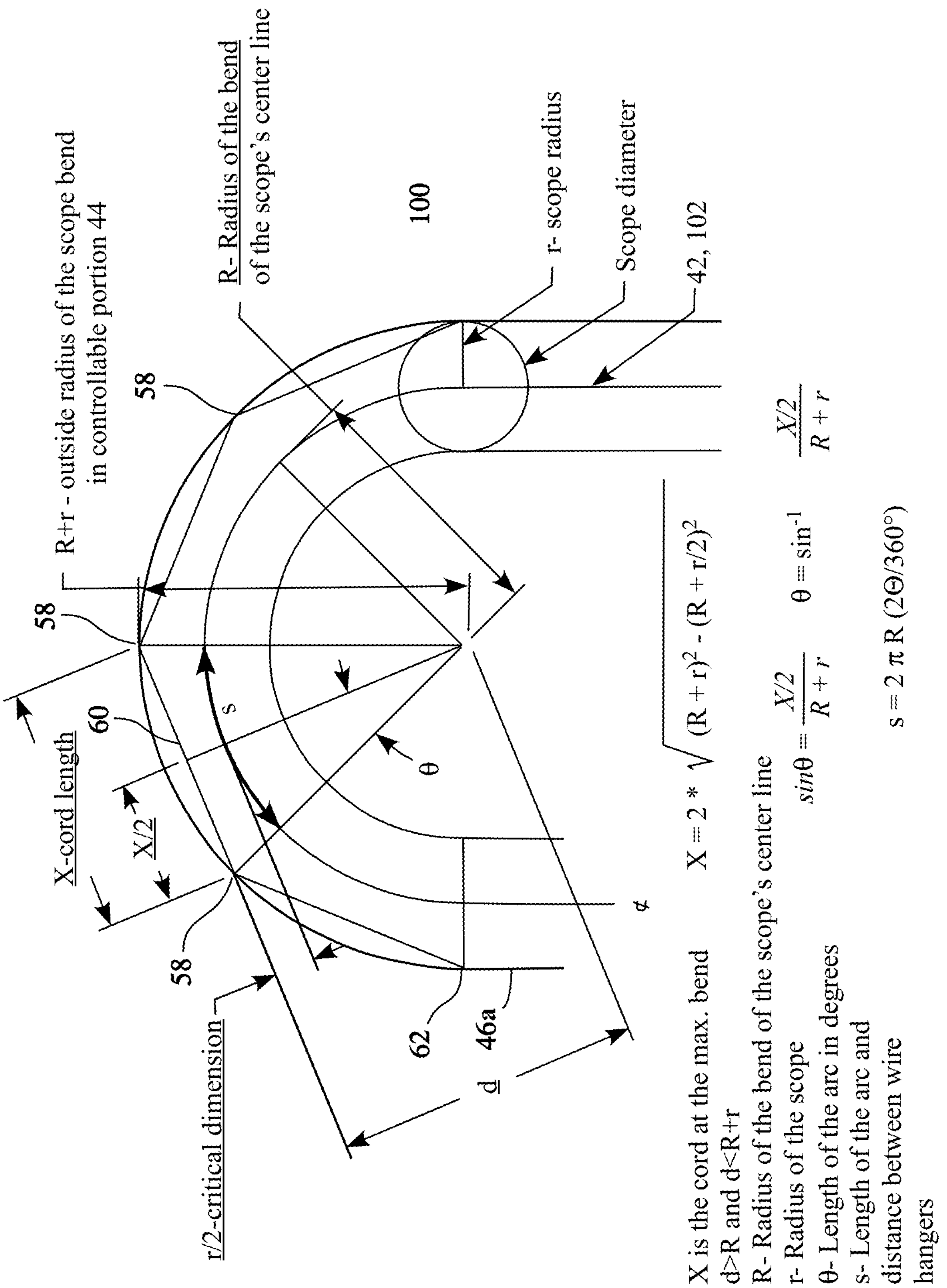
FIG. 9 illustrates how to calculate the maximum distance between two long-segments according to embodiments of this presentation.

According to embodiments of this presentation, the controllable section 44 of the endoscope may have a resilience sufficient to bring back the tube 32 toward an unbent state, after having pulled a wire 60 to bring the tube into a bent state and when releasing the wire 60. According to other embodiments of this presentation, however, the springiness of the controllable section 44 may not be enough and the endoscope must rely on the pull of one wire to unbend the tube after bending it in response to a pull on the other wire (in the case of endoscopes using two pull wires 60 as for example illustrated in FIGS. 2-8). The Inventors have noted that in order to always be able to unbend the tube with a first wire after bending the tube by pulling on the second wire, it is necessary that the first wire always remain on a same side of the sheet of points formed by the attachment sections 54. To achieve this, the loop structures 56 of the long-segments must not be distant by more than a maximum distance when the tube is in an unbent state. FIG. 9 illustrates how to calculate such maximum distance. As detailed above, the controllable section 44 of the endoscope is arranged such that pulling the proximal end of the tensioning wire brings closer the segments of the tube, which are separated by the cuts when the tube is in an unbent state and that have a same axial position as the loop openings, by flexing the attachment sections 54 between the segments of the tube. According to embodiments of this presentation, the controllable section 44 of the tube is arranged to achieve a maximally bent state when the attachment sections 54 between the segments of the tube are flexed sufficiently to let the segments of the tube that have a same axial position as the loop openings, touch each other instead of being separated by the cuts.

Figure 10:
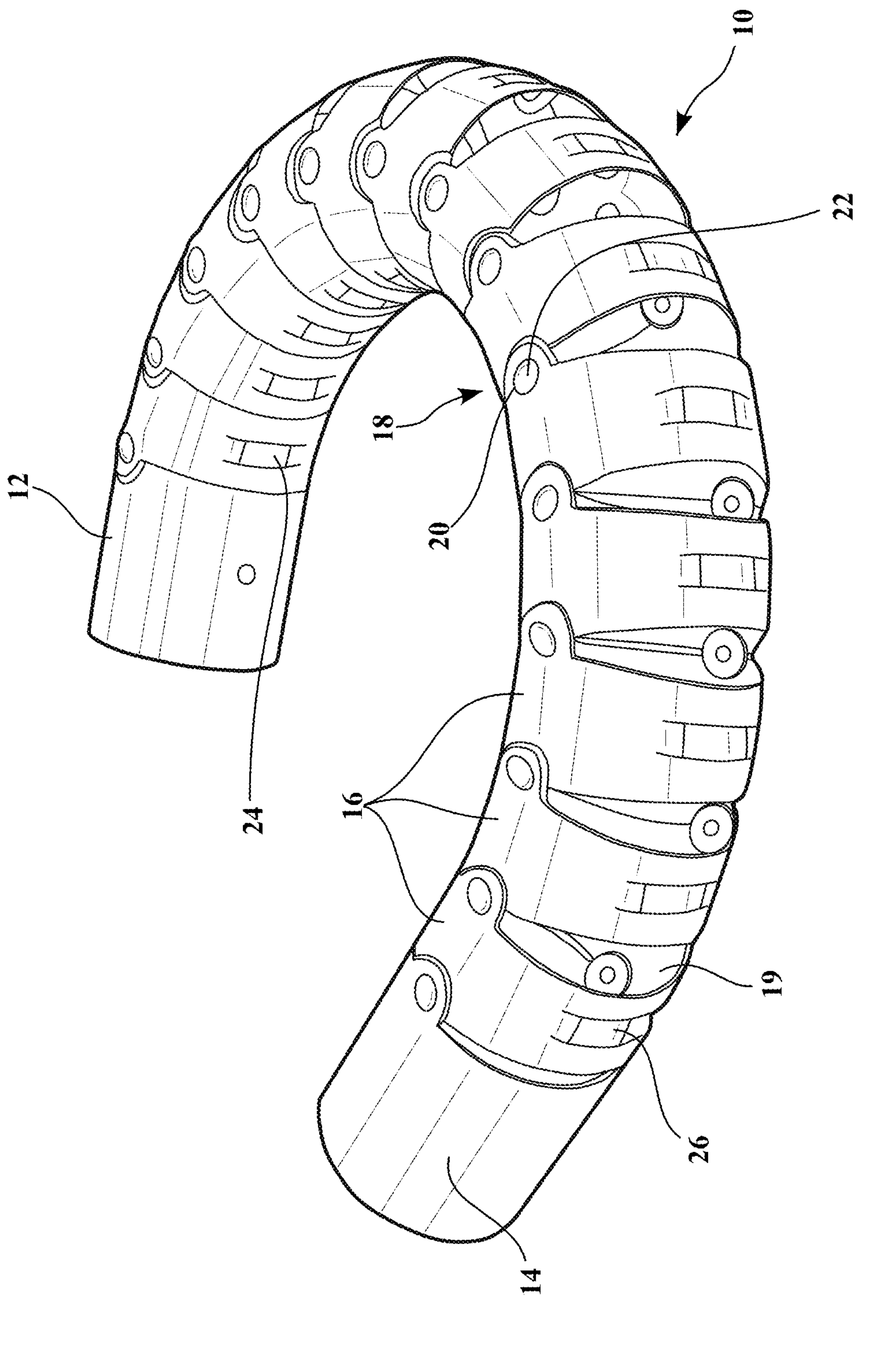
FIG. 10 is a perspective view of the endoscope of FIG. 4 in a bent position.

As detailed above and as illustrated in FIG. 10, in response to a pull wire 60 being pulled, the tube flexes along a flexure plane 100 which comprises both the axis of the tube and the pull wire 60 (not shown in FIG. 10). Plane 100 is materialized by the sheet of paper in FIG. 9. When the tube flexes, the sheet of points 102 formed by the attachment sections 54 flexes without being compressed. When attachment sections 54 are arranged symmetrically with respect to lumen axis 42, as illustrated in FIGS. 9 and 10, the sheet of points 102 formed by the attachment sections 54 includes the lumen axis 42. In FIG. 9, sheet of points 102 follows axis 42 and is normal to the sheet of paper. In other embodiments, the sheet of points 102 can be above or below the lumen axis 42.

According to embodiments of this presentation, the maximum distance between successive loop openings 58/loop structure 56, or between the secured distal end 62 of the at least one tensioning wire 60 and a closest loop opening 58/loop structure 56, when the controllable section 44 of the tube is in an unbent state, is chosen so that the tensioning wire 60 remains on a same side of the sheet of points 102 when bending the controllable section 44 of the tube from an unbent state to its maximally bent state.

According to embodiments of this presentation, in case the sheet of points 102 includes the lumen axis 42 as illustrated in FIG. 9, the maximal distance S between the centers of successive loop openings 58, or between the secured distal end 62 of the at least one tensioning wire 60 and a closest loop opening 58, when the controllable section of the tube is in an unbent state, is $$S=2\pi R(2\theta/360°);$$

where $$\theta=\sin^{-}[(X/2)/(R+r)];\text{ and}$$

$$X=2\sqrt{(R+r)^2-(R+r/2)^2};$$

R being the radius of a maximal bend of a line following the lumen axis of each segment of the tube, and r being the radius of the controllable section. The formulae above provide that the material of the tube is a substantially non-compressible material, for example metal. As outlined previously, the formulae above need to be applied when the tube does not provide sufficient springiness for the tube to unbend without wire pulling help when in use in a bodily cavity, and in case the sheet of points 102 includes the lumen axis 42.

Having now described the invention in accordance with the requirements of the patent statutes, those skilled in this art will understand how to make changes and modifications to the present invention to meet their specific requirements or conditions. Such changes and modifications may be made without departing from the scope and spirit of the invention as disclosed herein.

The foregoing Detailed Description of exemplary and preferred embodiments is presented for purposes of illustration and disclosure in accordance with the requirements of the law. It is not intended to be exhaustive nor to limit the invention to the precise form(s) described, but only to enable others skilled in the art to understand how the invention may be suited for a particular use or implementation. The possibility of modifications and variations will be apparent to practitioners skilled in the art.

No limitation is intended by the description of exemplary embodiments which may have included tolerances, feature dimensions, specific operating conditions, engineering specifications, or the like, and which may vary between implementations or with changes to the state of the art, and no limitation should be implied therefrom. Applicant has made this disclosure with respect to the current state of the art, but also contemplates advancements and that adaptations in the future may take into consideration of those advancements, namely in accordance with the then current state of the art. It is intended that the scope of the invention be defined by the Claims as written and equivalents as applicable. Reference to a claim element in the singular is not intended to mean "one and only one" unless explicitly so stated. Moreover, no element, component, nor method or process step in this disclosure is intended to be dedicated to the public regardless of whether the element, component, or step is explicitly recited in the Claims. No claim element herein is to be construed under the provisions of 35 U.S.C. Sec. 112, sixth paragraph, unless the element is expressly recited using the phrase "means for . . . " and no method or process step herein is to be construed under those provisions unless the step, or steps, are expressly recited using the phrase "comprising the step(s) of . . . ."

What is claimed is:

1. A controllable endoscope comprising a hollow tube having a distal end and a proximal end, the hollow tube comprising a tube wall surrounding a tube lumen having a lumen axis; a controllable section of the tube comprising an alternance of long-segments of the tube and flexible sections of the tube wherein:

the long-segments of the tube comprise a distal long-segment, a proximal long-segment, and n intermediate long-segments, wherein n is an integer at least equal to 1; each long-segment having a first axial length;

in each flexible section, the tube wall comprises a plurality of cuts along a series of planes perpendicular to the lumen axis, the cuts being arranged such that at least one uncut portion of the tube wall extends continuously in a direction parallel to the lumen axis between the distal end and the proximal end; wherein the plurality of cuts divide the tube wall in a series of short-segments of the tube, each short segment of the tube comprising a section of the uncut portion of the tube wall; the uncut portion of the tube wall effectively forming a series of attachment sections between the short segments of the tube, the uncut portion of the wall also forming attachment sections between the long segments of the tube and a closest neighboring short segment of the tube; each attachment section having a second axial length and each short-segment of the tube having a third axial length, wherein the first axial length is equal to or greater than three times the third axial length plus two times the second axial length; wherein the n intermediate long-segments and the proximal long-segment comprise each at least one loop structure protruding from the tube wall into the lumen, each loop structure having a loop opening parallel to the lumen axis, arranged to form at least one series of loop openings aligned in a direction parallel to the lumen axis when the controllable section of the tube is in an unbent state;

at least one tensioning wire having a distal end and a proximal end, the tensioning wire slidingly passing through the opening of the at least one series of loop structures, the distal end of the at least one tensioning wire being secured inside the lumen to the distal long-segment of the tube, such that controllably pulling the proximal end of the tensioning wire results in controllably bending the controllable section of the tube by flexing said attachment sections;

wherein the loop openings and the attachment sections have different radial positions, such that pulling the proximal end of the tensioning wire results in bringing closer portions of the segments of the tube, separated by the cuts when the tube is in an unbent state and that have a same axial position as the loop openings, by flexing the attachment sections between the segments of the tube;

wherein a distance between successive loop openings, or between the secured distal end of the at least one tensioning wire and a closest loop opening, when the controllable section of the tube is in an unbent state, is chosen so that the tensioning wire remains on a same side of a sheet of points, which includes the attachment sections that flex when bending the controllable section of the tube from an unbent state to the maximally bent state; and wherein the sheet of points includes the axis of the lumen, and wherein a maximal distance S, between successive loop openings, or between the secured distal end of the at least one tensioning wire and a closest loop opening, when the controllable section of the tube is in an unbent state, is $$S=2\pi R(\theta/360°);\text{ where}$$

$$\theta=\sin^{-1}[(X/2)/(R+r)];\text{ and}$$

$$X=2\sqrt{(R+r)^2-(R+r/2)^2};$$

with R being the radius of a maximal bend of a line following the lumen axis of each segment of the tube, and r being the radius of the controllable section.

* * * * *